United States Patent
Chen et al.

(10) Patent No.: US 12,207,919 B2
(45) Date of Patent: Jan. 28, 2025

(54) METHOD FOR HUMAN ACTION RECOGNITION IN HUMAN-MACHINE INTERACTIVE ASSEMBLY SCENE

(71) Applicant: TAIZHOU UNIVERSITY, Taizhou (CN)

(72) Inventors: Pengzhan Chen, Taizhou (CN); Lixian Wang, Taizhou (CN); Fang Li, Taizhou (CN)

(73) Assignee: TAIZHOU UNIVERSITY, Taizhou (CN)

( * ) Notice: Subject to any disclaimer, the term of this patent is extended or adjusted under 35 U.S.C. 154(b) by 256 days.

(21) Appl. No.: 17/820,918

(22) Filed: Aug. 19, 2022

(65) Prior Publication Data

US 2023/0233105 A1    Jul. 27, 2023

(30) Foreign Application Priority Data

Jan. 25, 2022 (CN) .......................... 202210085400.1

(51) Int. Cl.
    *A61B 5/11*    (2006.01)

(52) U.S. Cl.
    CPC .......... *A61B 5/1123* (2013.01); *A61B 5/1122* (2013.01)

(58) Field of Classification Search
    CPC ...... A61B 5/1123; A61B 5/1122; G06N 3/08; G06N 3/0464; G06N 3/045
    See application file for complete search history.

(56) References Cited

U.S. PATENT DOCUMENTS

| 10,258,259 | B1* | 4/2019 | Zets | A61B 5/7455 |
| 2014/0287389 | A1* | 9/2014 | Kallmann | G16H 20/30 434/247 |
| 2017/0103672 | A1* | 4/2017 | Dey | G06F 3/011 |
| 2021/0059565 | A1* | 3/2021 | Morris | G06V 40/25 |
| 2021/0086364 | A1* | 3/2021 | Handa | G06T 1/0014 |
| 2021/0335028 | A1* | 10/2021 | Yang | G06T 15/20 |
| 2022/0101603 | A1* | 3/2022 | Ni | G06V 40/103 |
| 2022/0143822 | A1* | 5/2022 | Bashkirov | G06N 3/088 |

FOREIGN PATENT DOCUMENTS

| CN | 106485055 B | * | 9/2017 | |
| CN | 113283373 A | * | 8/2021 | G06K 9/00342 |
| CN | 110321833 B | * | 5/2022 | G06K 9/00335 |

* cited by examiner

*Primary Examiner* — Eyob Hagos
(74) *Attorney, Agent, or Firm* — Schwegman Lundberg & Woessner, P.A.

(57) ABSTRACT

A method for human action recognition in a human-machine interactive assembly scene is disclosed in this application, joint coordinate streams of skeleton joints are obtained under a human action from motion sensing devices; a starting position and an ending position of the action are positioned according to data change based on a threshold value to obtain information of joints; resampling of angle change is made on the information of joints to obtain coordinates of joints; the coordinates of joints are normalized, to obtain a sequence of skeletons forming an action; obtaining a vector direction of the upper limb, and the scene is classified to be a left-hand scene or a right-hand scene; training is made for human action recognition in the left-hand scene and the right-hand scene respectively; human action outputs of the left-hand scene and the right-hand scene are fused to realize action recognition in a human-machine interaction scene.

7 Claims, 2 Drawing Sheets

METHOD FOR HUMAN ACTION RECOGNITION IN HUMAN-MACHINE INTERACTIVE ASSEMBLY SCENE

CROSS REFERENCE TO RELATED APPLICATION

This Non-provisional application claims priority under 35 U.S.C. § 119(a) to Chinese Patent Application No. 202210085400.1, filed on 25 Jan. 2022, the entire contents of which is hereby incorporated by reference in its entirety.

TECHNICAL FIELD

The disclosure relates to a technical field of human action recognition, in particular to a method for human action recognition in a human-machine interactive assembly scene.

BACKGROUND ART

A recognition method has been applied to in a single type of human-machine interactive assembly environment with a simple scene. Taking human-machine interactive assembly of a chair as an example, human is a dominant player in this assembly and a robot hands over chair accessories (such as a chair leg) and assembling tools (such as an Allen wrench) to the human as an assistant. The human and the robot can complete the assembly with only a few steps of interaction.

However, it presents a low action recognition accuracy and a slow recognition speed, and is prone to mistakes in recognition, resulting in low assembly efficiency.

SUMMARY

The present disclosure aims at solving one of technical problems in related art at least to a certain extent, in which a method for human action recognition in a human-machine interactive assembly scene is provided, which includes steps 1 to 7.

In the step 1, two motion sensing devices are provided. An included angle between the two motion sensing devices is a, and joint coordinate streams of skeleton joints are obtained under a human action from the motion sensing devices.

In the step 2, a joint coordinate stream with complete skeleton joints is screened out by a computer, and a starting position and an ending position of the action are positioned according to data change based on a threshold value (a joint data does not change at all before starting of the action and after ending of the action, but joint data changes significantly at a moment when the action starts or ends) to obtain information of joints.

In the step 3, resampling of angle change is made on the information of joints according to the included angle $\alpha$ to obtain coordinates of joints.

In the step 4, the coordinates of joints are normalized by taking coordinates of spinebase (joint 0) as an origin of a local coordinate system, and then smoothed to obtain a sequence of skeletons forming an action.

In the step 5, a vector of adjacent joints of an upper limb is simplified to obtain a vector direction of the upper limb, an included angle $\beta$ between vector directions of a left upper limb and a right upper limb and a vertical direction is respectively calculated, and the scene is classified to be a left-hand scene or a right-hand scene according to the included angle $\beta$.

In the step 6, the sequence of skeletons is inputted into a neural network, and training is made for human action recognition in the left-hand scene and the right-hand scene by the neural network respectively.

In the step 7, human action outputs of the left-hand scene and the right-hand scene are fused by a Softmax layer to realize action recognition in a human-machine interaction scene, so that a robot can assist a human to complete assembly actions.

Specifically, the included angle $\alpha$ between the two motion sensing devices is included angles between the two motion sensing devices and a horizontal direction.

Optionally, in this method, the motion sensing devices in the step 1 are Kinect sensors.

Optionally, in this method, the step 2 specifically is as follows. The start position and the end position of the action is detected according to the data change based on the threshold value. According to detection, an output signal is usually relatively stable before and after an action for the output signal occurs, but the signal at starting of the action instantaneously and significantly changes.

Optionally, in this method, the step 3 specifically is as follows. Resampling of the angle change is made at a $i^{th}$ coordinate of joints $(x_i^f, y_i^f, z_i^f)$ at $f^{th}$ frames before the angle change, and made at a coordinate of joints $\overline{P}_i^f(\overline{x}_i^f, \overline{y}_i^f, \overline{z}_i^f)$ after the angle change, with a coordinate transformation relation being as follows.

$$\overline{P}_i^f = \begin{bmatrix} x_i^f \\ y_i^f \\ z_i^f \end{bmatrix}^T \begin{bmatrix} 0 & 1 & 0 \\ \cos\alpha & 0 & 0 \\ 0 & 0 & \sin\alpha \end{bmatrix}, f \in N$$

$\alpha$ is determined according to the included angle between two Kinect sensors, $f \in N$, $i \in [1,17]$.

Optionally, in this method, the step 4 specifically is as follows. The coordinates of spinebase (joint 0) is taken as the origin of the local coordinate system, and the coordinates of spinebase is subtracted from coordinates of each joint in each frame, as shown below:

$$\tilde{x}_i^f = x_i^f - x_{spinebase}^f$$

$$\tilde{y}_i^f = y_i^f - y_{spinebase}^f$$

$$\tilde{z}_i^f = z_i^f - z_{spinebase}^f$$

where $(\tilde{x}_i^f, \tilde{y}_i^f, \tilde{z}_i^f)$ is coordinates of a $i^{th}$ joint in a $f^{th}$ frame after normalization, here $i \in [1,17]$; $(x_{spinebase}^f, y_{spinebase}^f, z_{spinebase}^f)$ is three-dimensional coordinates of the spinebase in a $f^{th}$ frame, which is processed to obtain the sequence of skeletons $F_i \in R^{C^{in} \times T \times V}$, where $C^{in}$ is a number of input channels, T is a number of skeletons in the sequence, and V is a number of joints of each skeleton.

Optionally, in this method, the step 5 specifically is as follows. Elbow Right is defined as a point B, Wrist Right is defined as a point C, ElbowLeft is defined as a point E and WristLeft is defined as a point F. With Shoulder Right being defined as a point A and ShoulderLeft being defined as a point D, then vectors of the upper limb is simplified as $\overrightarrow{AB}$, $\overrightarrow{AC}$, $\overrightarrow{DE}$, $\overrightarrow{DF}$, and the included angle $\beta_1$, $\beta_2$ between the vector direction of the upper limb or $\overrightarrow{AB}$ or $\overrightarrow{DE}$ and the vertical direction is calculated. It can be classified to be the left-hand scene or the right-hand scene with a determination basis of $\beta_1$, $\beta_2$ being within a predetermined range. The predetermined range is 15° to 90° (because an angle in which an arm swings is within this range during the human-machine interactive assembly). Specifically, a recognition rate is lowest with $\beta_1$, $\beta_2$ being 45°.

Optionally, in this method, it can be classified to be the left-hand scene or the right-hand scene with a determination basis of being between 15 to 90 degrees, which is specifically as follows. A human skeleton data sequence $F_i \in R^{c^{in} \times T \times V}$ is input and a prediction function is constructed as follows:

$$h_\theta(F_i) = g\left(\beta^T F_i\right) = \frac{1}{1 + e^{-\theta^T F_i}}$$

where g represents a logarithmic probability function, T represents transposing, and e represents a base. $\theta$ is an angle change value of $\beta$.

A predicted value A1 at a first time is obtained using an initially set parameter assigned with a value of 0. When probability is greater than or equal to 60%, an output is y=1, which indicates the left hand scene, whereas the output is y=0 which indicates the right hand scene.

Additional aspects and advantages of the disclosure will be set forth in part in the following description, and in part will be obvious from the following description, or may be learned by practice of the disclosure.

With the included angle $\beta$ between vector directions of the left upper limb and the right upper limb and the vertical direction, the scene can be classified to be the left hand scene or the right hand scene according to the angle $\beta$. Then, in a single and separate scene, a simplified lightweight convolutional neural network is trained to perform human action recognition until recognition accuracy and loss rate meet requirements. Finally, output results of the two scenes (for example, if the result of scene segmentation is the left-hand scene, which specific action on the left-hand side is trained in the database on the left-hand) are combined to realize a final action recognition in the human-machine interaction scene. Compared with current methods for human action recognition in simple scenes, the method according to the disclosure has better action recognition accuracy and speed, and compared with most of methods based on deep learning, it has less reasoning time, thus improving computational efficiency.

DETAILED DESCRIPTION

Figure 1:
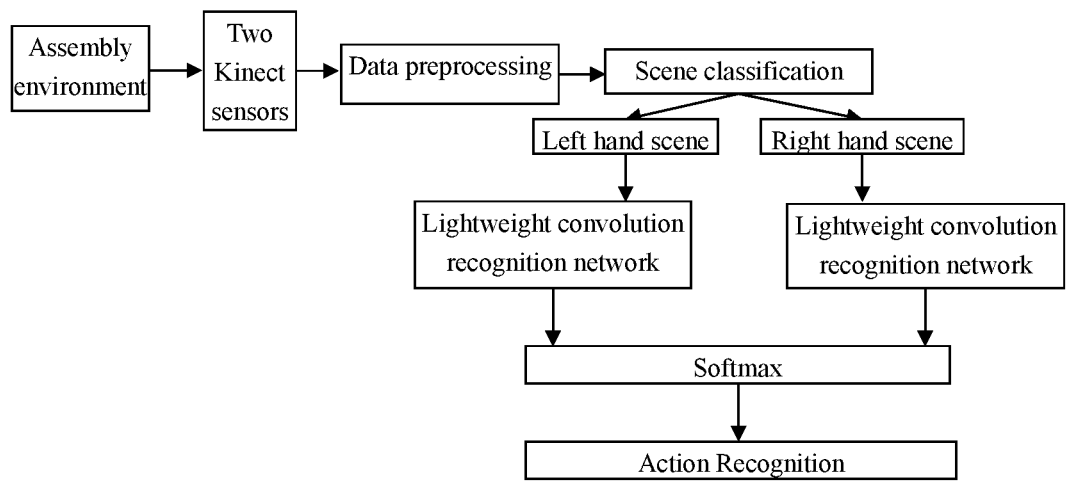
FIG. 1 is a flow diagram of a method for human action recognition in a human-machine interactive assembly scene according to the present disclosure.

Embodiments of the present disclosure will be described in detail below, examples of which are shown in the accompanying drawings, in which same or similar reference numerals refer to same or similar elements or elements with same or similar functions throughout. The embodiments described below with reference to the drawings are exemplary and are intended to explain the present disclosure, but should not be construed as limiting the present disclosure.

A method for human action recognition in a human-machine interactive assembly scene according to an embodiment of the present disclosure will be described in detail below with reference to the drawings.

Embodiment 1

As shown in FIG. 1, a method for human action recognition in a human-machine interactive assembly scene includes steps 1 to 7.

In the step 1, two motion sensing devices are provided. An included angle between the two motion sensing devices is a, and joint coordinate streams of skeleton joints are obtained under a human action from the motion sensing devices.

In the step 2, a joint coordinate stream with complete skeleton joints is screened out by a computer, and a starting position and an ending position of the action are positioned according to data change based on a threshold value to obtain information of joints.

In the step 3, resampling of angle change is made on the information of joints according to the included angle $\alpha$ to obtain coordinates of joints; In the step 4, the coordinates of joints are normalized by taking coordinates of spinebase (joint 0) as an origin of a local coordinate system, and then smoothed to obtain a sequence of skeletons forming an action, In the step 5, a vector of adjacent joints of an upper limb is simplified to obtain a vector direction of the upper limb, an included angle $\beta$ between vector directions of a left upper limb and a right upper limb and a vertical direction is respectively calculated, and the scene is classified to be a left-hand scene or a right-hand scene according to the included angle $\beta$.

In the step 6, inputting the sequence of skeletons into a neural network, and training is made for human action recognition in the left-hand scene and the right-hand scene by the neural network respectively.

In the step 7, human action outputs of the left-hand scene and the right-hand scene are fused by a Softmax layer to realize action recognition in a human-machine interaction scene, so that a robot can assist a human to complete assembly actions.

With the included angle $\beta$ between vector directions of the left upper limb and the right upper limb and the vertical direction, the scene can be classified to be the left hand scene or the right hand scene according to the angle $\beta$. Then, in a single and separate scene, a simplified lightweight convolutional neural network is trained to perform human action recognition until recognition accuracy and loss rate meet requirements. Finally, outputs of the two scenes are fused to realize the final action recognition in the human-machine interactive scene. Compared with current methods for human action recognition in simple scenes, the method according to the disclosure has better action recognition accuracy and speed, and compared with most of methods based on deep learning, it has less reasoning time, thus improving computational efficiency.

The motion sensing devices in the step 1 can be Kinect sensors, and there are two tripods which are fixed and placed in a height range of 1 to 2 m (because this range can cover heights of all the experimental participants) in the scene. When the height is the same as that of a person, the two sensors located in front of an operator form a certain angle with a horizontal direction. The Kinect sensors record coordinate streams of 25 human skeleton joints at a frame rate of 30 Hz.

Figure 2:
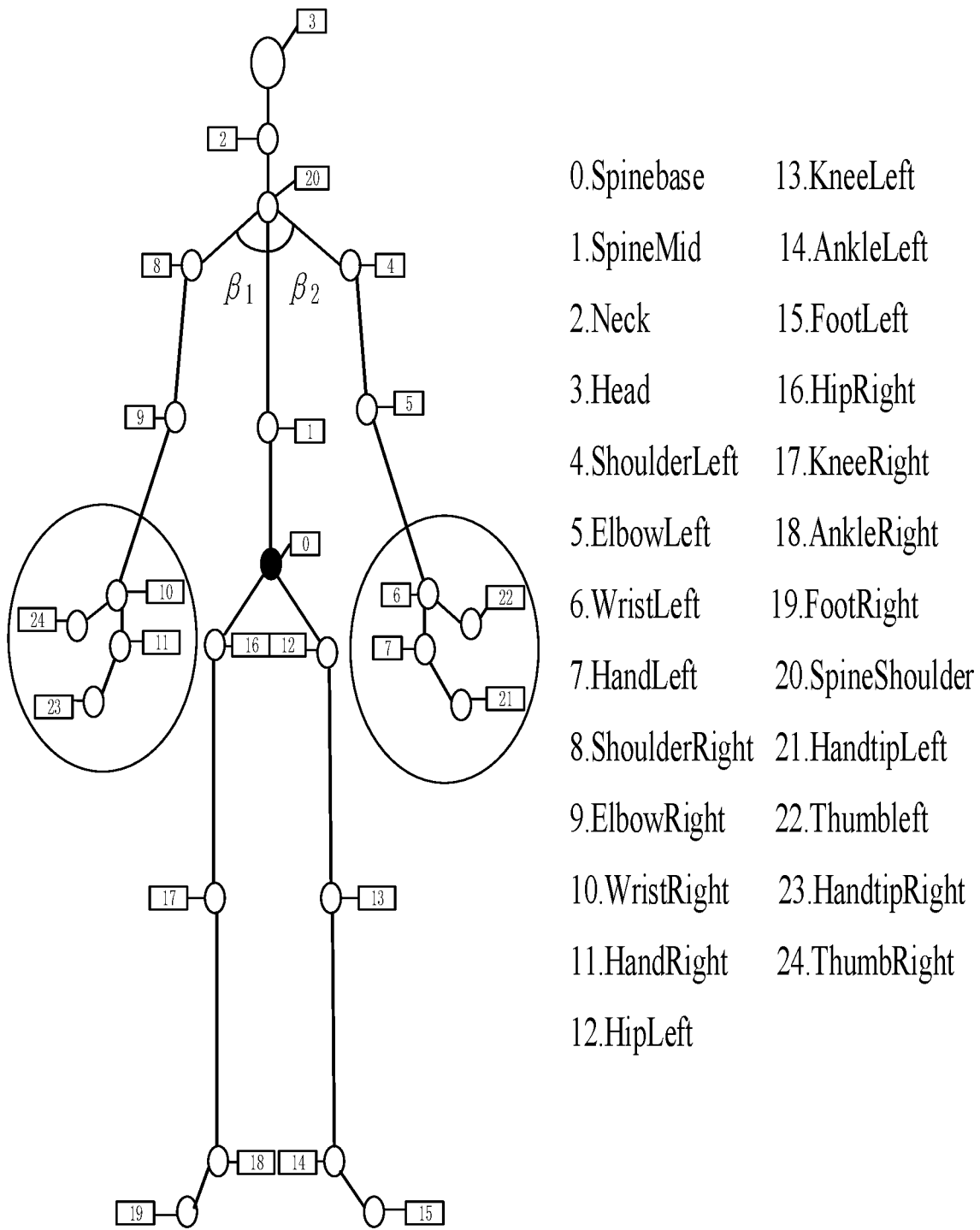
FIG. 2 is a skeleton joint diagram of a method for human action recognition in a human-machine interactive assembly scene according to the present disclosure.

As shown in FIG. 2, coordinates of the 25 skeleton joints are specifically as follows: 0. Spine base; 1. Spine mid; 2. Neck; 3. Head; 4. Shoulder Left; 5. Elbow Left; 6. Wrist Left; 7. Hand Left; 8. Shoulder Right; 9. Elbow Right; 10. Wrist Right; 11. Hand Right; 12. Hip Left; 13. Knee Left; 14. Ankle Left; 15. Foot Left; 16. Hip Right; 17. Knee Right; 18. Ankle Right; 19. Foot Right; 20. Spine Shoulder; 21. Handtip Left; 22. Thumb Left; 23. Handtip Right; 24. Thumb Right.

The step 2 specifically is as follows. The start position and the end position of the action is detected according to an action event segmentation algorithm. According to detection, an output signal is usually relatively stable before and after an action for the output signal occurs, but the signal at starting of the action instantaneously and significantly changes.

The step 3 specifically is as follows. Resampling of the angle change is made at a $i^{th}$ coordinate of joints $(x_i^f, y_i^f, z_i^f)$ at $f^{th}$ frames before the angle change, and made at a coordinate of joints $(\bar{x}_i^f, \bar{y}_i^f, \bar{z}_i^f)$ after the angle change, with a coordinate transformation relation being as follows.

$$\bar{x}_i^f = x_i^f \cos \theta$$

$$\bar{y}_i^f = y_i^f$$

$$\bar{z}_i^f = z_i^f \sin \theta$$

where $\theta$ is determined according to the included angle between two Kinect sensors, $f \in N$, $i \in [1,17]$.

The step 4 specifically is as follows. The coordinates of spinebase (joint 0) is taken as the origin of the local coordinate system, and the coordinates of spinebase is subtracted from coordinates of each joint in each frame, as shown below:

$$\tilde{x}_i^f = x_i^f - x_{spinebase}^f$$

$$\tilde{y}_i^f = y_i^f - y_{spinebase}^f$$

$$\tilde{z}_i^f = z_i^f - z_{spinebase}^f$$

where $(\tilde{x}_i^f, \tilde{y}_i^f, \tilde{z}_i^f)$ is coordinates of a $i^{th}$ joint in a $f^{th}$ frame after normalization, here $i \in [1,17]$, $(x_{spinebase}^f, y_{spinebase}^f, z_{spinebase}^f)$ is three-dimensional coordinates of the spinebase in the $f^{th}$ frame. After normalization, all three-dimensional coordinates of the spinebase become 0, and this joint is removed in calculating, with a total number of joints of 16. Finally, a Gaussian filter is configured to smooth original data of each dimension. This is implemented in Python. The processed sequence of skeletons is $F_i \in R^{c^{in} \times T \times V}$, where $c^{in}$ is a number of input channels, T is a number of skeletons in the sequence, and V is a number of joints of each skeleton. Then, the sequence of skeletons is modeled as a time-space diagram, and the sequence of skeletons is a one-dimensional time series structure.

The step 5 specifically is as follows. Elbow Right is defined as a point B, Wrist Right is defined as a point C, Elbow Left is defined as a point E and Wrist Left is defined as a point F. With Shoulder Right being defined as a point A and Shoulder Left being defined as a point D, then vectors of the upper limb is simplified as $\overrightarrow{AB}$, $\overrightarrow{AC}$, $\overrightarrow{DE}$, $\overrightarrow{DF}$, and the included angle $\beta_1$, $\beta_2$ between the vector direction of the upper limb $\overline{AB}$ or $\overline{DE}$ and the vertical direction (that is, a human torso, which is a line of a hip circumference center, spine, cervical spine, neck and head) is calculated. It can be classified to be the left-hand scene or the right-hand scene with a determination basis of $\beta_1$, $\beta_2$ being between 15 to 90 degrees.

With a basic principle of Logistic Regression, a suitable prediction function (a $\lambda$ function) is found. The $\lambda$ function is configured to predict a determination result of input data. For example, when a value of 15° is taken, it is classified to be the left-hand scene; otherwise, it is classified to be the right-hand scene.

With the sequence of skeletons as an input and a scene classification result as an output. A Logistic Regression model is constructed as follows:

1. The sequence of human skeletons $F_i$ is input, the prediction function is constructed as follows. A predicted value A1 at a first time is obtained using an initially set parameter assigned with a value of 0 (there is no limit in logistic that all parameters can't be initially set to be 0, which exist in a neural network with a hidden layer). When probability is greater than or equal to 60%, an output y=1, which indicates the left hand scene, whereas the output y=0 which indicates the right hand scene.

$$h_\theta(F_i) = g\left(\theta^T F_i\right) = \frac{1}{1 + e^{-\theta^T F_i}}$$

where g represents a logarithmic probability function, T represents transposing, and e represents a base. $\theta$ is an angle change value of $\beta$.

2. A loss function is constructed, and a cost function of logistic regression is calculated with a corresponding label $\beta$ in a training set, with the cost function and the function being as follows:

$$\text{Cost}(h_\theta(F_i), y) = \begin{cases} -\log(h_\theta(F_i)) & \text{if } y = 1 \\ -\log(1 - h_\theta(F_i)) & \text{if } y = 0 \end{cases}$$

$$J(\theta) = \frac{1}{m}\sum_{i=1}^{m} \text{Cost}(h_\theta(F_i), y_i) = -\frac{1}{m}\left[\sum_{i=1}^{m}(y_i h_\theta(F_i) + (1 - y_i)\log(1 - h_\theta(F_i)))\right]$$

where a cost function is a logarithmic probability function, which correspondingly outputs probability of a positive sample; the function is a log-likelihood function; m is a maximum value of the $(x_i, y_i)$ data set and $\theta$ is an angle change value of $\beta$.

3. Iteration is made for a next calculation according to a gradient descent algorithm, to get the updated W and $\theta$ value, and the cost function is calculated again until the loss function is close to 0, which indicates that the training is almost complete.

4. Get the W and $\theta$ value after training is complete, and performance is tested using a test set.

The scene classification result obtained in step 5 is taken as a known condition, if it is the left hand scene, the space-time sequence of skeletons with joint coordinates of the left shoulder, left arm, left wrist, left hand, left thumb, left tip, hip circumference center, spine, cervical vertebra, neck and head is taken as an input into a lightweight convolutional neural network which consists of a convolution layer, an activation function layer, a pool layer, a local response normalization layer, a normalization layer and a final fully connected layer (with a number of nodes of 300). The activation function is ReLu, a number of convolution kernels is 32, the loss function is selected as categorical_crossentropy, the optimization function is Adam, with measurement indexes of accuracy and loss. Model parameters are constantly adjusted, and adjusting the model parameters is stopped when the recognition accuracy reaches above 95% and the loss rate drops below 5%. On the contrary, when the result of the step 5 is the right hand scene, operations are similar to those of the left hand scene, and a space-time sequence of skeletons with right-hand joint coordinates is input correspondingly. Models for both scenes are trained separately, so that they can reach training targets respectively.

Finally, outputs of the two scenes are fused by a Softmax layer to realize the final action recognition in the human-machine interactive scene. The left-hand scene and the right-hand scene can be firstly classified, which has better action recognition accuracy and speed, and compared with most of methods based on deep learning, it has less reasoning time, thus improving the computational efficiency. Finally, outputs of the two scenes are fused to realize the final action recognition in the human-machine cooperation scene. The recognition accuracy and speed are better.

Additional aspects and advantages of the disclosure will be set forth in part in the following description, and in part will be obvious from the following description, or may be learned by practice of the disclosure.

With the included angle between vector directions of the left upper limb and the right upper limb and the vertical direction, the scene can be classified to be the left hand scene or the right hand scene according to the angle. Then, in a single and separate scene, a simplified lightweight convolutional neural network is trained to perform human action recognition until recognition accuracy and loss rate meet requirements. Finally, outputs of the two scenes are fused to realize the final action recognition in the human-machine interactive scene. Compared with current methods for human action recognition in simple scenes, the method according to the disclosure has better action recognition accuracy and speed, and compared with most of methods based on deep learning, it has less reasoning time, thus improving computational efficiency.

In the description of this specification, description referring to terms "one embodiment", "some embodiments", "examples", "specific examples" or "some examples" means that specific features, structures, materials or characteristics described in connection with this embodiment or example are included in at least one of embodiments or examples of the present disclosure. In this specification, schematic expressions of the above terms do not necessarily refer to a same embodiment or example. Furthermore, the specific features, structures, materials or characteristics described may be combined in any one or more of embodiments or examples in a suitable manner. In addition, those skilled in the art can incorporate and combine different embodiments or examples or features of different embodiments or examples described in this specification without mutual inconsistence.

Although the embodiments of the present disclosure have been shown and described above, it is to be understood that the above embodiments are illustrative and should not be construed as limitations of the present disclosure, and changes, modifications, substitutions and variations to the above embodiments can be made by those skilled in the art within the scope of the present disclosure.

For those skilled in the art, upon reading the above description, various changes and modifications will undoubtedly be obvious. Therefore, the appended claims should be regarded as covering all changes and modifications of true intention and scope of the disclosure. Any and all equivalent ranges and contents within the scope of the claims should be considered as still falling within the intention and scope of the present disclosure.

What is claimed is:

1. A method for human action recognition in a human-machine interactive assembly scene, comprising:

step 1, providing two motion sensing devices, an included angle between the two motion sensing devices being $\alpha$, and obtaining joint coordinate streams under a human action from the motion sensing devices;

step 2, screening out a joint coordinate stream with complete skeleton joints by a computer, and positioning a starting position and an ending position of the action according to data change based on a threshold value to obtain information of joints;

step 3, resampling angle change on the information of joints according to the included angle $\alpha$ to obtain coordinates of joints;

step 4, normalizing the coordinates of joints by taking coordinates of spinebase as an origin of a local coordinate system, and then smoothing to obtain a sequence of skeletons forming an action;

step 5, simplifying a vector of adjacent joints of an upper limb to obtain a vector direction of the upper limb, calculating an included angle $\beta$ between vector directions of a left upper limb and a right upper limb and a vertical direction respectively, and classifying the scene to be a left-hand scene or a right-hand scene according to the included angle $\beta$;

step 6, inputting the sequence of skeletons into a neural network, and training for human action recognition in the left-hand scene and the right-hand scene by the neural network respectively; and step 7, assembling, with a robot, a human-machine interaction scene, based on fusing human action outputs of the left-hand scene and the right-hand scene by a Softmax layer to realize action recognition, causing the robot to assist a human in completing assembly actions.

2. The method for human action recognition in the human-machine interactive assembly scene according to claim 1, wherein the motion sensing devices in the step 1 are Kinect sensors.

3. The method for human action recognition in the human-machine interactive assembly scene according to claim 1, wherein the step 2 specifically comprises: detecting the start position and the end position of the action according to the data change based on the threshold value, according to detection, an output signal being stable before and after an action for the output signal occurs, and the signal at starting of the action instantaneously and significantly changing.

4. The method for human action recognition in the human-machine interactive assembly scene according to claim 1, wherein the step 3 specifically comprises: resampling the angle change at a $i^{th}$ coordinate of joints $(x_i^f, y_i^f, z_i^f)$ at $f^{th}$ frames before the angle change, and made at a coordinate of joints $\overline{P}_i^f(\overline{x}_i^f, \overline{y}_i^f, \overline{z}_i^f)$ (after the angle change, with a coordinate transformation relation being as follows:

$$\overline{P}_i^f = \begin{bmatrix} x_i^f \\ y_i^f \\ z_i^f \end{bmatrix}^T \begin{bmatrix} 0 & 1 & 0 \\ \cos\alpha & 0 & 0 \\ 0 & 0 & \sin\alpha \end{bmatrix}, f \in N$$

where $\alpha$ is the included angle between two motion sensing devices, $f \in N, i \in [1,17]$.

5. The method for human action recognition in the human-machine interactive assembly scene according to claim 1, wherein the step 4 specifically comprises: taking the coordinates of spinebase as the origin of the local coordinate system, and subtracting the coordinates of spinebase from coordinates of each joint in each frame, as shown below:

$$\tilde{x}_i^f = x_i^f - x_{spinebase}^f$$

$$\tilde{y}_i^f = y_i^f - y_{spinebase}^f$$

$$\tilde{z}_i^f = z_i^f - z_{spinebase}^f$$

where $(\tilde{x}_i^f, \tilde{y}_i^f, \tilde{z}_i^f)$ is coordinates of a $i^{th}$ joint in a $f^{th}$ frame after normalization, here $i \in [1,17]$; $(x_{spinebase}^f, y_{spinebase}^f, z_{spinebase}^f)$ is three-dimensional coordinates of the spinebase in a $f^{th}$ frame, which is processed to obtain the sequence of skeletons $F_i \in R^{c^{in} \times T \times V}$, where $C^{in}$ is a number of input channels, T is a number of skeletons in the sequence, and V is a number of joints of each skeleton.

6. The method for human action recognition in the human-machine interactive assembly scene according to claim 1, wherein the step 5 specifically comprises: defining ElbowRight as a point B, WristRight as a point C, ElbowLeft as a point E, WristLeft as a point F, ShoulderRight as a point A and ShoulderLeft as a point D, and simplifying vectors of the upper limb as $\vec{AB}, \vec{AC}, \vec{DE}, \vec{DF}$, and the included angle $\beta_1, \beta_2$ between the vector direction of the upper limb or $\vec{AB}$ or $\vec{DE}$ and the vertical direction, and classifying to be the left-hand scene or the right-hand scene with a determination basis of $\beta_1, \beta_2$ being within a predetermined range.

7. The method for human action recognition in the human-machine interactive assembly scene according to claim 6, wherein the classifying to be the left-hand scene or the right-hand scene with a determination basis of $\beta_1, \beta_2$ being within a predetermined range comprises: inputting a human skeleton data sequence and constructing a prediction function as follows:

$$h_\theta(F_i) = g(\beta^T F_i) = \frac{1}{1 + e^{-\theta^T F_i}}$$

$$\text{Cost}(h_\theta(F_i), y) = \begin{cases} -\log(h_\theta(F_i)) & \text{if } y = 1 \\ -\log(1 - h_\theta(F_i)) & \text{if } y = 0 \end{cases}$$

$$J(\theta) = \frac{1}{m} \sum_{i=1}^{m} \text{Cost}(h_\theta(F_i), y_i) = -\frac{1}{m} \left[ \sum_{i=1}^{m} (y_i h_\theta(F_i) + (1 - y_i) \log(1 - h_\theta(F_i))) \right]$$

where g represents a logarithmic probability function, T represents transposing, and e represents a base, θ is an angle change value of β, and a cost function is a logarithmic probability function, which correspondingly outputs probability of a positive sample; a J function is a log-likelihood function; and m is a maximum value of the $(x_i, y_i)$ data set; and obtaining a predicted value A1 at a first time using an initially set parameter assigned with a value of 0, when probability is greater than or equal to 60%, an output being y=1, which indicates the left hand scene, whereas the output being y=0 which indicates the right hand scene.

* * * * *